United States Patent
Thiel et al.

(10) Patent No.: US 7,986,415 B2
(45) Date of Patent: Jul. 26, 2011

(54) APPARATUS AND METHOD FOR OPTICAL 3D MEASUREMENT

(75) Inventors: Frank Thiel, Ober Ramstadt (DE); Joachim Pfeiffer, Bensheim (DE); Peter Fornoff, Reichelsheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 0 days.

(21) Appl. No.: 12/506,531

(22) Filed: Jul. 21, 2009

(65) Prior Publication Data

US 2009/0279103 A1 Nov. 12, 2009

Related U.S. Application Data

(63) Continuation of application No. PCT/EP2008/050787, filed on Jan. 24, 2008.

(30) Foreign Application Priority Data

Jan. 31, 2007 (DE) .......................... 10 2007 005 726

(51) Int. Cl.
*G01B 11/24* (2006.01)
(52) U.S. Cl. ....................................... 356/608
(58) Field of Classification Search .................. 356/601, 356/608; 250/559.22
See application file for complete search history.

(56) References Cited

U.S. PATENT DOCUMENTS

| | | | | |
|---|---|---|---|---|
| 3,812,505 A * | 5/1974 | Elliott | | 396/21 |
| 5,613,936 A * | 3/1997 | Czarnek et al. | | 600/166 |
| 5,737,084 A * | 4/1998 | Ishihara | | 356/609 |
| 6,263,234 B1 | 7/2001 | Engelhardt et al. | | |
| 6,564,087 B1 | 5/2003 | Pitris et al. | | |
| 6,564,089 B2 | 5/2003 | Izatt et al. | | |
| 6,697,164 B1 * | 2/2004 | Babayoff et al. | | 356/609 |
| 6,885,464 B1 | 4/2005 | Pfeiffer et al. | | |
| 6,940,611 B2 * | 9/2005 | Babayoff et al. | | 356/609 |
| 7,184,150 B2 * | 2/2007 | Quadling et al. | | 356/602 |
| 2004/0090638 A1* | 5/2004 | Babayoff et al. | | 356/609 |
| 2005/0264828 A1 | 12/2005 | Babayoff et al. | | |
| 2007/0153296 A1 | 7/2007 | Schick | | |

FOREIGN PATENT DOCUMENTS

| | | |
|---|---|---|
| DE | 196 40 495 A1 | 4/1998 |
| DE | 198 29 278 C1 | 2/2000 |
| EP | 1 797 813 A1 | 6/2007 |
| JP | 1-313712 A | 12/1989 |
| WO | 00/08415 | 2/2000 |

* cited by examiner

*Primary Examiner* — Roy Punnoose
(74) *Attorney, Agent, or Firm* — Fitzpatrick, Cella, Harper & Scinto (57) ABSTRACT

The invention relates to an apparatus and a method for optical 3D measurement, comprising a first beam deflector for deflecting an illuminating beam onto a measurement object and for deflecting the observation beam which is radiated back by the measurement object, wherein the first beam deflector can move along a path distance S.

36 Claims, 2 Drawing Sheets

APPARATUS AND METHOD FOR OPTICAL 3D MEASUREMENT

CROSS REFERENCE TO RELATED APPLICATIONS

This application is a continuation of International Application No. PCT/EP2008/050787, filed Jan. 24, 2008, which claims priority to German Patent Application No. 10 2007 005 726.3, filed Jan. 31, 2007, each of which is incorporated by reference herein in its entirety, as if set forth fully herein.

The present invention relates to an apparatus and method for optical 3 D measurement.

PRIOR ART

A number of devices for optical 3 D measurement are known in the prior art. In many cases, the optical 3 D measurement is carried out by optically scanning the surfaces of an object to be measured with the aid of one or more light beams. The surfaces can be scanned by means of a point light beam or one or more stripes of light.

Devices are well-known in which linear scanning is carried out by using a stripe of light to scan the surface in a direction extending at right angles to the stripe of light.

These devices often function on the basis of a chromatic confocal measuring method, a classical confocal measuring method with mechanical depth scan, a triangulation measuring method, a classical interferometry measuring method, a white-light interferometry measuring method, or a deflectometry measuring method.

In the chromatic confocal measuring method, a polychromatic point source of light is imaged on an object to be measured by means of a so-called chromatic objective depending on the wavelength of the light. The reflected light is analyzed spectrally behind a diaphragm by means of a color sensor such as a spectrometer or a CCD camera. Based on the spectral distribution of the reflected light, it is possible to determine the relative position of the object to be measured in the z direction normal to the surface of the object to be measured.

In a classical confocal measuring method with mechanical depth scan, the focal position is altered by mechanical scanning of the optics or of the object relative to the optics.

In the triangulation measuring method, an single light beam or a plurality of stripes of light, which may be parallel for example, are projected onto an object to be measured and moved perpendicularly to the direction of the stripes of light. The reflected light is then detected by means of an image sensor such as a CCD camera. The distance from the object to be measured can be determined from the position and angle of the projection beam and a reflected monitoring beam relative to the object to be measured by the use of trigonometric methods of calculation.

In the classical interferometry measuring method, information concerning the object to be measured is acquired by means of an interferometer by way of the physical effect of interference. The illuminating beam is superimposed on the monitoring beam reflected by the object to be measured by means of an interferometer to form an interferogram. The prerequisite for successful interference is that the light beams be superimposed coherently. This means that the light beams coming from various directions can interfere only if the path lengths of the two light beams differ from each other by less than the coherence length. The coherence length is dependent on the wavelength and spectral bandwidth of the light used.

The white-light interferometry measuring method utilizes the interference of a broadband light such as that of white light. This measuring method compares the delay time of the monitoring beam reflected by the object to be measured with the aid of an interferometer such as a Michelson interferometer with the delay time of the illuminating beam having a known optical path length as reference. The interference of the two light beams results in a pattern from which the relative optical path length can be derived.

In the deflectometry measuring method, the image of a light pattern, such as that of a grid, is observed in the reflection across the surface of the object to be measured. The local gradients of the surface can be determined from the deformation of the grid image, and the 3 D information of the object to be measured can be produced from the local gradients.

In devices known in the prior art, the scanning movement of the light beams is carried out, for example, by means of a rotating mirror inside a housing of the apparatus. The rotating mirror is turned about an axis of rotation extending normal to the direction of the light beam and it deflects the light beam by oscillating within an angular range. The oscillating light beam is then deflected onto the surface of the object to be measured by a beam deflector immovably mounted at the front end of the apparatus.

DE 198 29 278 C1 discloses a 3 D camera for recording surface structures, more particularly for dental purposes. The direction of a projection beam is altered with the aid of a diaphragm and the projection beam is deflected onto the object to be measured by means of a prism disposed at the front end of the apparatus. A monitoring beam reflected by the object to be measured is in turn deflected via the prism and guided to an image sensor for image analysis.

A disadvantage of such devices is that a mirror or a prism is used for deflecting the projection beam or monitoring beam toward the object to be measured and for deflecting the reflected monitoring beam toward the image sensor, which is stationarily installed. Its dimensions thus substantially determine the size of the potential scan area of such devices. The scan area is the area that is scanned on the object to be measured with the aid of the projection beam and the monitoring beam. A mirror or prism used must be large enough to enable the projection beam and monitoring beam to be deflected onto the object to be measured within the scan area. Therefore, in the case of a large scan area, the overall height of the devices is correspondingly large and is, in particular, a hindrance to 3 D measurement of teeth in the oral cavity of a patient.

It is thus an object of the present invention to provide a 3 D measuring apparatus which has a small overall height and at the same time allows for scanning of the largest possible scan area.

SUMMARY OF THE INVENTION

This object is achieved by the present invention.

According to the invention, the optical 3 D measuring apparatus comprises a first beam deflector for deflecting an illuminating beam onto an object to be measured and for deflecting the monitoring beam reflected by said object, the first beam deflector being movable through a path distance S.

The first beam deflector can be in the form of, say, a deflection mirror, a deflecting prism or any other device which acts on a light beam so as to change its direction.

The apparatus can be used for implementation of known optical measuring methods, such as the chromatic confocal measuring method, the triangulation measuring method, the classical interferometry measuring method, the white-light interferometry measuring method, and the deflectometry measuring method.

The illuminating beam can be both monochromatic and polychromatic depending on the measuring method used. When using a monochromatic illuminating beam for the triangulation measuring method, classical interferometry measuring method, white-light interferometry measuring method, or deflectometry measuring method, the illuminating beam need not necessarily be focused. If the illuminating beam is not focused, only the first beam deflector is moved through the path distance S without any optical focusing system such as an objective. Otherwise, the illuminating beam will be focused by means of an optical focusing system such as an objective, which is moved together with the first beam deflector.

The first beam deflector moving through the path distance S deflects the illuminating beam onto the object to be measured, the radiated illuminating beam remaining unchanged. Thus a scanning movement of the illuminating beam is carried out by moving the first beam deflector through the path distance S. The first beam deflector can be moved, for example, linearly through a path distance S parallel to the direction of the radiated illuminating beam so that a scan area having the length S is scanned on the object. The illuminating beam impinges on the object and is partially reflected due to reflecting and scattering processes and is guided by the first beam deflector as a monitoring beam back to the image sensor for image signal analysis.

3 D measurement of a scan area can be accomplished with the aid of a single scan by way of the monitoring beam. If the illuminating beam is in the form of a stripe, the 3 D measurement can be carried out by means of a single scanning movement at right angles to the direction of the stripe. This single scanning movement is generated by a single movement of the first beam deflector through the path distance S. A plurality of light stripes or other light patterns can also be used as the illuminating beam. An illuminating point beam is required to perform the scanning movement several times in order to scan a scan area line by line.

The first beam deflector is movable, unlike in prior devices, which have an immovably mounted beam deflector for deflecting the monitoring beam. The direction of the illuminating beam remains unchanged. The first beam deflector must thus be of small dimensions in order to deflect the monitoring beam. The overall height of the apparatus can consequently be lower than that of prior devices so that in dental applications, in particular, access to teeth inside an oral cavity is greatly facilitated.

A further advantage is that the apparatus of the invention makes it possible to scan a larger scan area of length S, since the length of the path S is limited only by the overall length of the apparatus.

An objective for focusing the illuminating beam can be moved concurrently together with the first beam deflector as it is moved through the path distance S.

In the chromatic confocal measuring method, the polychromatic illuminating beam is focused on the surface of the object so that an objective has to be moved concurrently together with the first beam deflector in order to keep the focal point in a plane extending parallel to the direction of movement of the first beam deflector at a constant focal length of the objective. When using a polychromatic illuminating beam for the other optical 3 D measurement methods such as the triangulation measuring method, the classical interferometry measuring method, the white-light interferometry measuring method, or the deflectometry measuring method, the illuminating beam must also be focused, thus necessitating an objective that is likewise moved concurrently with the first beam deflector.

The beam deflector can advantageously be moved through the path distance S in an oscillatory manner.

If the illuminating beam is a point beam, it can scan the scan area line by line in an oscillatory manner during 3 D measurement. Such a scanning movement is generated by the oscillating movement of the beam deflector through the path distance S.

If the illuminating beam is in the form of a stripe, a single scanning movement is sufficient for scanning a scan area having the width of the stripe. Such a 3 D scan can also be carried out in an oscillatory manner in order to obtain the respective surface information in a continuous manner. This is significant in the case of objects to be measured that change over time. In the case of such oscillatory 3 D measurement, the apparatus can be moved around the object to be measured in order to obtain surface information therefrom from a number of directions. The individual 3 D images created from various directions can then be assembled to form a complete 3 D image of the object.

3 D measurement of a scan area can be accomplished by a single scan by means of the monitoring beam. In the case of an illuminating beam that is in the form of a stripe, for example, 3 D measurement can be carried out by means of a single scanning movement at right angles to the stripe, which scanning movement is generated by a single movement of the first beam deflector through the path distance S.

The first beam deflector can advantageously be guided linearly over the path distance S within the housing of the apparatus with the aid of guide means. The degrees of freedom of the first beam deflector are thus limited to a linear movement.

A counterweight in a force-balancing unit can be advantageously moved contrary to the motion of the first beam deflector so that the forces and torques arising from the motion of the first beam deflector and those arising from the counterweight counterbalance each other as far as possible.

The force-balancing unit comprises a counterweight which is mounted inside the housing of the apparatus and is moved contrarily to the first beam deflector. Depending on the acceleration and the weight moved, there result acceleration forces which cause torques as the vector product of force and distance from the pivot. For example, the counterweight can have the same weight as the first beam deflector plus its concurrently moved mounting parts so that when the counterweight and the beam deflector are moved in contrary directions at an acceleration of equal value, contrary acceleration forces result that counterbalance each other. The acceleration forces act on points of which the orthogonal distances from the pivot are substantially equal to each other so that the torques likewise almost counterbalance each other. The points of action of the acceleration forces are the centers of gravity of the weights moved, namely the first beam deflector plus its mounting parts and the counterweight. The force-balancing unit consequently prevents vibration of the apparatus during 3 D measurement which otherwise would have to be compensated by the user and would render vibration-free scanning impossible.

The counterweight can advantageously be guided linearly in a direction opposite to the linear movement of the first beam deflector inside the housing of the apparatus with the aid of guide means. The beam deflector and the counterweight are thus guided in the desired directions and over the desired path distance S.

The movement of the counterweight can advantageously be coupled to that of the first beam deflector with the aid of coupling means. The counterweight thus need not be driven separately and synchronized by complicated means with the drive provided for the linear movement of the first beam deflector. The advantage of mechanical coupling is that the movements of the first beam deflector and the counterweight remain synchronized even in the case of a possible unforeseen change in frequency.

The coupling means can advantageously be toothed wheels, toothed racks, springs and/or resilient fibers. The movements are thus coupled to each other mechanically in a simple manner.

Advantageously, the path distance S can be between 1 mm and 40 mm. It is thus possible to scan a scan area having a length S between 1 mm and 40 mm. Thus certain sections of a row of teeth can be scanned for creating 3 D images in the oral cavity of a patient.

Advantageously, the oscillating movement of the first beam deflector can take place at a frequency ranging from 1 Hz to 100 Hz. To achieve rapid 3 D measurement, the frequency of the scanning movement should be adjusted to be as high as possible. However, the processing speed of the image sensor is a factor limiting the frequency of the scanning movement.

Advantageously, the first beam deflector can be part of a scanning unit that can be moved in an oscillatory manner inside the housing of the apparatus. The first beam deflector can be located, for example, inside a transparent scanning unit which is made of Plexiglas and potted together with the first beam deflector. The first beam deflector can alternatively be permanently connected to the scanning unit in other ways. Thus the entire scanning unit performs the preferably linear oscillatory scanning movement together with the beam deflector inside the apparatus. The weight of the counterweight must thus be configured such that the acceleration force of the entire scanning unit is counterbalanced. For example, the weight of the counterweight can be equal to that of the scanning unit. A further alternative would be a counterweight of lesser or greater weight but having a stronger or weaker acceleration, in order to provide a counterbalancing acceleration force.

Advantageously, the scanning unit can comprise a plurality of beam deflectors in order to deflect the illuminating beam a number of times. The optical path of the illuminating beam can thus be deflected inside the housing of the apparatus in the desired manner, as a result of which the apparatus can be designed in various ways.

Advantageously, the scanning unit can comprise an objective for focusing the illuminating beam onto the surface of the object to be measured. The objective is moved concurrently with the first beam deflector in the scanning unit so that the parallel illuminating beams are focused onto the surface of the object to be measured. The focal length of the objective is thus equal to the distance from the principal plane of the objective along the optical axis to the first beam deflector and from the first deflector to the focal point on the surface of the object to be measured. The counterweight can be equal to the weight of the scanning unit plus that of the objective in order to counterbalance the acceleration force.

Advantageously, the objective can be a chromatic objective and the illuminating beam can be focused onto the surface of the object to be measured depending on wavelength. A chromatic objective is used in the chromatic confocal measuring method for 3 D measurement. The focal length changes as a function of the wavelength of the radiated light photons so that only a limited spectral range of the radiated polychromatic light is sharply focused onto the surface of the object to be measured. A spectral analysis of the reflected light then gives information concerning the relative position of the object to be measured along the central axis of a beam.

Advantageously, the apparatus can comprise a connector for a fiber-optic light guide, which connects the apparatus to a base unit, the fiber-optic light guide being adapted to guide the illuminating beam from a light source disposed in the base unit to the apparatus and to guide the monitoring beam reflected by the object back to the base unit, which monitoring beam is deflected by means of a beam splitter and then analyzed. The apparatus can thus be moved independently of the base unit. The base unit comprises the light source, the beam splitter disposed downstream of the light source and a light sensor such as a spectrometer or a CCD camera for analyzing the reflected light. Furthermore, the apparatus can be configured with smaller external dimensions and less weight so as to facilitate the use thereof and to improve the access thereof to an object such as teeth, more particularly inside an oral cavity, in dental applications.

Advantageously, the first beam deflector can be disposed on that end of the apparatus that is remote from the connector for the fiber-optic light guide. This facilitates access to the molar teeth, in particular.

Advantageously, the first beam deflector can be at an angle of 45° relative to the illuminating beam, so that the latter is deflected at right angles. The apparatus must thus be held normal to the surface of the objective. The optical 3 D measurement of tooth surfaces is thus improved, since tooth surfaces reflect the illuminating beam mainly diffusely in all directions across the tooth surface with the preferential direction of maximum intensity extending perpendicularly to the tooth surface.

Advantageously, the illuminating beam can consist of a series of component beams disposed in a plane. Parallel 3 D measurement can thus be carried out by means of the component beams so that the time taken for scanning is reduced. If a chromatic confocal measuring method is used, a plurality of juxtaposed point component beams disposed in a row can be used, which are individually focused by means of the chromatic objective disposed in the optical path of the component beams, while the reflected monitoring beams are imaged confocally on a color sensor by means of appropriately disposed diaphragms.

Advantageously, the optical 3 D measuring apparatus can be a dental handpiece for scanning tooth surfaces in the oral cavity of a patient. The apparatus of the invention can therefore be used for dental purposes.

Advantageously, the first beam deflector can be shifted between two positions, the first beam deflector deflecting the illuminating beam in a first direction in the first position while, in the second position, it deflects the illuminating beam in a second direction that is contrary to the first direction.

In the first position, the illuminating beam can be deflected in the first direction, for example, toward the teeth of the lower jaw, and in the second position in the second direction, for example, toward the teeth of the upper jaw. Thus the direction of 3 D measurement by the apparatus can be altered without having to turn the apparatus. The shift from the first position to the second position can be effected by rotating the beam deflector about an axis extending normal to the illuminating beam.

In a first direction of polarization, the first beam deflector can advantageously deflect the linearly polarized illuminating beam in the first direction, and in the second direction of polarization it can deflect the beam in a second direction contrary to the first direction.

In a first direction of polarization, the linearly polarized illuminating beam is deflected in the first direction, and it is deflected in the second direction in a second direction of polarization. Such a polarization-dependent beam deflector can consist, for example, of a polarizing filter and a deflection mirror disposed downstream thereof in the optical path of the illuminating beam. If the polarization of the illuminating beam is at right angles to the transmission direction of the polarizing filter, the illuminating beam is reflected almost entirely by the polarizing filter and is deflected in the first direction. If the polarization of the illuminating beam is parallel to the transmission direction of the polarizing filter, the illuminating beam passes therethrough almost entirely and is then reflected by the deflection mirror disposed downstream of the polarizing filter and thus deflected in the second direction contrary to the first direction.

Advantageously, the angle of the first beam deflector relative to the direction of the illuminating beam can be variable.

A desired deflecting angle of the illuminating beam can thus be set such that scan areas that are located in front of the apparatus and are difficult to access can also be scanned.

A further object of the present invention is a method for optical 3 D measurement using an apparatus comprising a first beam deflector, wherein an illuminating beam is deflected onto an object to be measured by means of the first beam deflector moved through a path distance S and a monitoring beam reflected by the object is also deflected.

A scanning movement of the illuminating beam is thus caused by the scanning movement of the first beam deflector, which can be moved, for example, linearly over a path distance S parallel to the direction of the illuminating beam. A scan area having the length S can thus be scanned on the object to be measured.

An advantage of the method is that a relatively large scan area having the length S can be scanned, since the first beam deflector is moved along the apparatus of the invention and thus is limited only by the overall length of the apparatus.

A further advantage of the method is that everywhere in the scan area having the length S the illuminating beam impinges on the surface of the object at the same angle relative to the apparatus. The intensity of the reflected beam is thus easier to compare, since the intensity of the reflected light is angle-dependent for diffuse reflection.

Advantageously, the first beam deflector can be moved through the path distance S in an oscillatory manner.

The oscillatory scanning movement generated by the oscillating movement of the first beam deflector enables a scan of a scan area to be carried out line by line using an illuminating point beam, or permits continuous scanning of an object that changes over time or scanning of an object from various directions.

Advantageously, the beam deflector can be moved linearly through the path distance S. The illuminating beam is thus deflected at all points of the path distance S at the same angle.

Advantageously, a counterweight in a force-balancing unit can be moved in an oscillatory manner contrarily to the first beam deflector so that the forces and torques arising during the movements of the first beam deflector and those arising from the counterweight counterbalance each other as far as possible. The weight of the counterweight can be the same as that of the first beam deflector plus its mounting parts that are moved therewith so that when the counterweight and the beam deflector are moved in opposite directions, there result acceleration forces that counterbalance each other. The acceleration forces act on points of the apparatus having an equal orthogonal distance from a pivot so that the torques likewise counterbalance each other. The force-balancing unit thus prevents vibration of the apparatus during 3 D measurement which would otherwise have to be compensated by the user and would render vibration-free scanning impossible.

Advantageously, the counterweight can be moved linearly contrary to the motion of the first beam deflector. The counterweight can thus be moved contrarily to the likewise linear movement of the first beam deflector.

Advantageously, the path distance S can range from 1 mm to 40 mm. This allows for 3 D measurement of a row of teeth over a distance ranging from 1 mm to 40 mm.

Advantageously, the oscillating movement of the first beam deflector can take place at a frequency ranging from 1 Hz to 100 Hz. The frequency of the scanning movement should be adjusted to be as high as possible in order to achieve rapid 3 D measurement. The processing speed of the image sensor, such as a spectrometer or CCD camera, limits the frequency of the scanning movement to that possible for imaging the monitoring beam.

Advantageously, the illuminating beam can be deflected a number of times by additional beam deflectors disposed in the optical path upstream of the first beam deflector. The optical path of the illuminating beam can thus be deflected a number of times inside the apparatus and diverted at any desired angle relative to the surface of the object to be measured.

Advantageously, the illuminating beam can be focused by an objective onto the surface of the object to be measured. The surface of the object to be measured is thus located at the focal point of the objective and is imaged sharply. The weight of the objective as a component of the oscillatory scanning unit contributes to the acceleration force of the scanning unit.

Advantageously, the first beam deflector can deflect the illuminating beam at right angles. The apparatus can thus be held parallel to the surface of the object, the illuminating beam impinging perpendicularly onto the surface of the object to be measured. This is advantageous particularly for 3 D measurement of teeth due to the difficulty in accessing the same. When the illuminating beam is radiated perpendicularly, the intensity of the reflected light is at its highest, since the tooth surfaces reflect light diffusely with the maximum intensity extending perpendicularly to the tooth surface.

Advantageously, the radiated polychromatic illuminating beam can be focused by an objective onto the surface of the object to be measured as a function of the wavelength. The objective focuses radiated polychromatic light to focal points that are wavelength dependent so that only a limited spectral range is sharply focused on the surface of the object to be measured and the remaining spectral ranges form only out-of-focus images of the surface.

Advantageously, the illuminating beam can consist of a series of component beams disposed in a plane. 3 D measurement can thus be carried out in parallel using the series of component beams so that the time taken for scanning is reduced.

The object to be measured by optical 3 D measurement can advantageously be a tooth surface in the oral cavity of a patient. The method of the invention can thus be used for dental purposes.

Advantageously, the first beam deflector can be shifted between two modes, in which the first beam deflector deflects the illuminating beam in a first direction in the first mode and deflects the illuminating beam in a second direction contrary to the first direction in the second mode. The direction of scanning can thus be altered without turning the apparatus.

BRIEF DESCRIPTION OF THE DRAWINGS

Exemplary embodiments of the invention are illustrated in the drawings, in which.

EXEMPLARY EMBODIMENTS OF THE INVENTION

Figure 1:
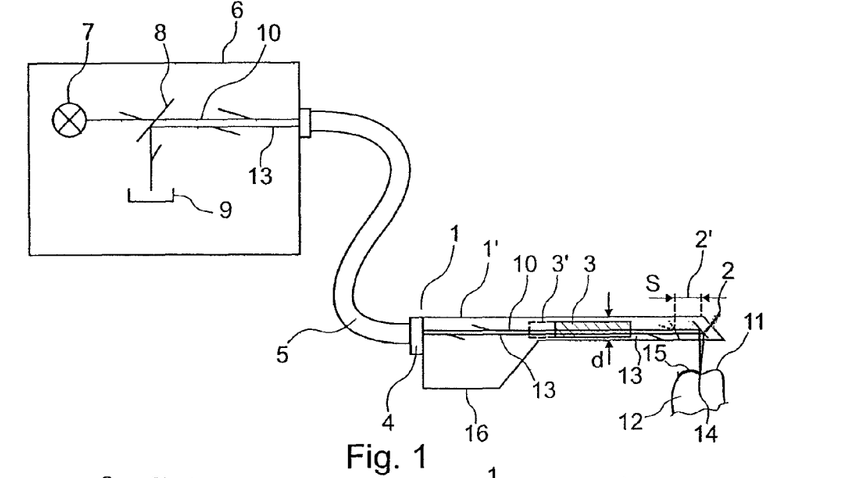
FIG. 1 is an overall view of the 3 D measuring apparatus comprising a dental handpiece and a base unit.

FIG. 1 shows an optical 3 D measuring apparatus 1 comprising a first beam deflector 2, an objective 3 and a connector 4 for a fiber-optic light guide 5. The first beam deflector 2 can be oscillated over a path distance S. The first beam deflector 2', indicated by dashed lines, shows the position of the beam deflector 2 following linear movement thereof through the path distance S. The objective 3 is likewise moved together with the first beam deflector 2 linearly along the path S. The objective 3', indicated by the dashed lines, shows the position of the objective 3 following movement thereof. The illustrated optical 3 D measuring apparatus 1 has the form of a dental handpiece that is connected to a base unit 6 by means of a fiber-optic light guide 5. The base unit 6 comprises a light source 7, a beam splitter 8, and an image sensor 9. A radiated light beam 10, which is generated by the light source 7, attenuated by the beam splitter 8 and guided by the fiber-optic light guide 5 to the dental handpiece 1', is focused in the handpiece 1' by the objective and deflected by the first beam deflector 2 onto the surface 11 of an object 12 to be measured. In the present case, the object to be measured is a single tooth in the oral cavity of a patient. The radiated light beam 10 is reflected by the surface 11 of the tooth 12. The amount of light diffusely reflected is greater than the amount of directional reflected light. In the case of diffuse reflection, the reflected light is radiated in all directions across the illuminated surface, the maximum intensity of the reflected light being radiated perpendicularly to the surface. In the case of directional reflection, the angle of incidence to the surface is equal to the angle of reflection.

A part of the mainly diffusely reflected light thus travels back to the first beam deflector and is deflected by the same in the form of a monitoring beam 13 toward the objective 3. The reflected light beam 13 is converted in the objective 3 back to beams extending parallel to each other and the reflected light beam 13 travels through the fiber-optic light guide 5 back to the base unit 6. In the base unit 6, a part of the monitoring beam 13 is deflected by the beam splitter 8 toward the image sensor. The objective 3 focuses the radiated light beam 10 onto the surface 11 of the object 12 to be measured such that the focal point 14 of the objective 3 is located on the surface 11. As a result of the oscillatory, linear scanning movement of the first beam deflector 2 over the path distance S, it is possible to optically scan a scan area 15. From the perspective of the illuminating beam 10, the scan area 15 thus has a length equal to that of the path distance S. In the case illustrated, the path distance S is 10 mm and the apparatus is thus suitable for scanning a single tooth. Devices can also be constructed, the mechanics of which allow a scanning movement along a longer path distance S for scanning larger scan areas. The frequency of the scanning movement can be selected so as to range from 1 Hz to 100 Hz. A higher frequency would reduce the time taken for scanning but would have to be selected so as not to exceed the maximum frequency at which the image sensor 9 can process the incoming imaging signals. The apparatus 1 is encased by a housing 16.

Alternatively, the apparatus of the invention can be formed as a stationary or mobile apparatus in a housing enclosing all components, including the light source and the image sensor, while a data cable for transferring the image data connects such apparatus to an image analyzing unit.

The illuminating beam 10 can have the form of a point of light, a stripe of light or a projection comprising a plurality of stripes, or have some other form. The illuminating beam 10 can be a monochromatic light-beam or a polychromatic light beam depending on the 3 D measurement method employed.

Figure 2:
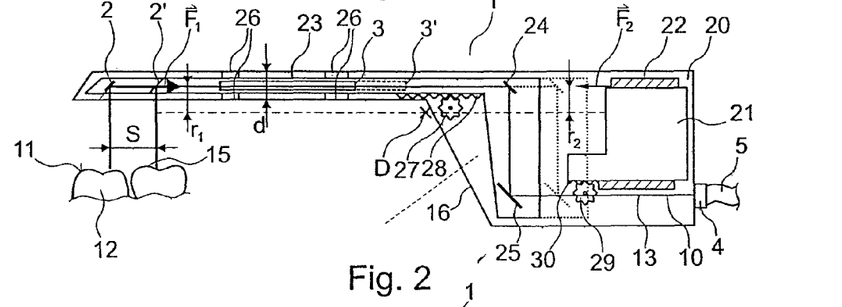
FIG. 2 is a detailed view of the dental handpiece comprising a scanning unit and a force-balancing unit.

FIG. 2 shows an optical 3 D measuring apparatus 1 as shown in FIG. 1 and comprising a force-balancing unit 20. The force-balancing unit 20 comprises a counterweight 21 and guide means 22. The counterweight 21 is guided by means of guide means 22 contrary to the oscillatory linear scanning movement of the first beam deflector 2. In contrast to FIG. 1, the first beam deflector 2 is mounted in a scanning unit 23 which also comprises the objective 3 and two additional beam deflectors 24 and 25. The first beam deflector 2' and the objective 3', indicated by dashed lines, show the respective positions of the beam deflector 2 and the objective 3 following the scanning movement through the path distance S. The scanning unit 23 is guided by means of guide means 26 in the dental handpiece 1'. The counterweight 21 has the same weight as the scanning unit 23 and is moved synchronously contrary to the scanning unit so that acceleration forces $F_1$ of the scanning unit and acceleration forces $F_2$ of the counterweight 21 counterbalance each other. The acceleration forces $F_1$ and $F_2$ act at points, the paths $r_1$ and $r_2$ of which from the pivotal point D are equal so that the torque $M_1$ as the vector product of $F_1$ and $r_1$ is counterbalanced by the torque $M_2$ as a vector product of $F_2$ and $r_2$. The force-balancing unit 20 is thus used for balancing the acceleration force $F_1$ and the torque $M_1$ and thus prevents vibration of the apparatus 1 during 3 D measurement, which would otherwise have to be compensated by the user and would render vibration-free 3 D measurement impossible.

The scanning unit 23 can be cast, for example together with the objective 3 and the beam deflectors 2, 24, and 25, as a single unit from transparent Plexiglas. The oscillatory linear scanning movement is effected by the drive of a toothed wheel 27, which engages in a toothed rack 28 disposed on the scanning unit 23. The countermovement of the counterweight 21 is brought about by an additional drive of a toothed wheel 29, which engages in a toothed rack 30 disposed on the counterweight 21. The drives of the toothed wheels 27 and 29 are synchronized with each other in order to ensure movements with contrary accelerations and acceleration forces $F_1$ and $F_2$. The radiated light beam 10 travels, as in FIG. 1, through the fiber-optic light guide 5 through the connector 4 into the apparatus 1 and is deflected by the beam deflectors 25 and 24 disposed in the scanning unit 23 and is focused in the objective 3 and deflected by the first beam deflector 2 onto the surface 11 of the object 12 to be measured The reflected light beam 13 is then guided, as in FIG. 1, through the same path back to the image sensor 9.

A special advantage of the apparatus 1 of the invention over devices known in the prior art is that scanning of the scan area 15 of length S is carried out by means of the oscillatory linear scanning movement of the first beam deflector 2. The first beam deflector 2 can thus be constructed with small dimensions since it is required to deflect the radiated light beam 10, the orientation of which remains unchanged throughout 3 D measurement. Consequently, the installation height d of the apparatus 1 can also be kept small enough to facilitate access to objects to be measured, such as teeth in the oral cavity of a patient. In prior devices, the position of the first beam deflector relative to the apparatus remains unchanged and the scanning movement is carried out by turning the illuminating beam 10 by means of a rotating mirror mounted in the optical path in front of the first beam deflector so that the length of the scan area substantially determines the installation height of the apparatus. The object 12 to be measured and illustrated in FIG. 1 is part of a row of teeth composed of two adjacent teeth. The apparatus 1 shown in FIG. 1 and FIG. 2 can be used for 3 D scanning carried out by means of the chromatic confocal scanning method, the triangulation scanning method, the fringe projection scanning method, and other optical methods.

Figure 3:
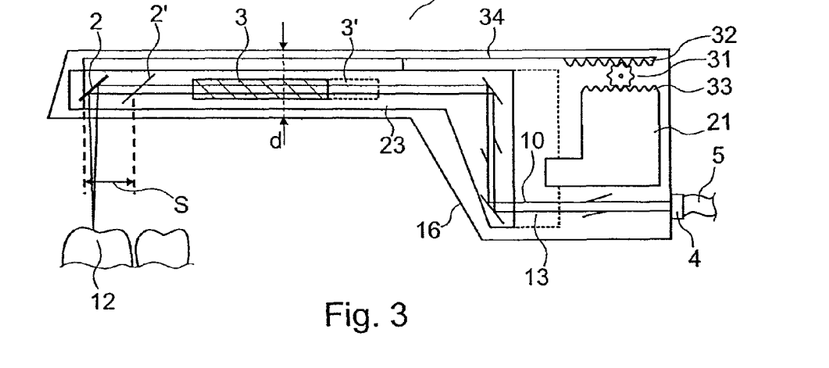
FIG. 3 is a detailed view of the dental handpiece shown in FIG. 2 comprising coupling means between the force-balancing unit and the scanning unit.

FIG. 3 shows the apparatus 1 shown in FIG. 2, the movements of the scanning unit 23 being coupled to the first beam deflector 2 and the counterweight 21 with the aid of coupling means, namely a driving toothed wheel 31, a toothed rack 32 and a toothed rack 33. The toothed rack 32 is connected via a connecting part 34 to the scanning unit 23 which comprises the first beam deflector 2. The toothed rack 33 is mounted on the counterweight 21. The drive of the toothed wheel 31 brings about the oscillatory linear scanning movement of the scanning unit 23 and the countermovement of the counterweight 21 contrary thereto so that the forces $F_1$, $F_2$ and the torques $M_1$, $M_2$ indicated in FIG. 2 counterbalance each other. The advantage of the coupling as compared with the apparatus shown in FIG. 2 is that the counterweight 21 and the scanning unit 23 need not be driven independently of each other and the drives of the toothed wheels 27 and 29 need not be synchronized, which is cost-saving.

Similar to the apparatus shown in FIG. 2, the apparatus 1 shown in FIG. 3 can be used for various 3 D measurement methods requiring an oscillating light beam or a stripe of light for acquiring surface information. The radiated light beam 10 travels, as in FIG. 2, via the fiber-optic light guide 5 into the apparatus 1 and the reflected light beam is guided by means of the fiber-optic light guide 5 back to the base unit 6 shown in FIG. 1.

Figure 4:
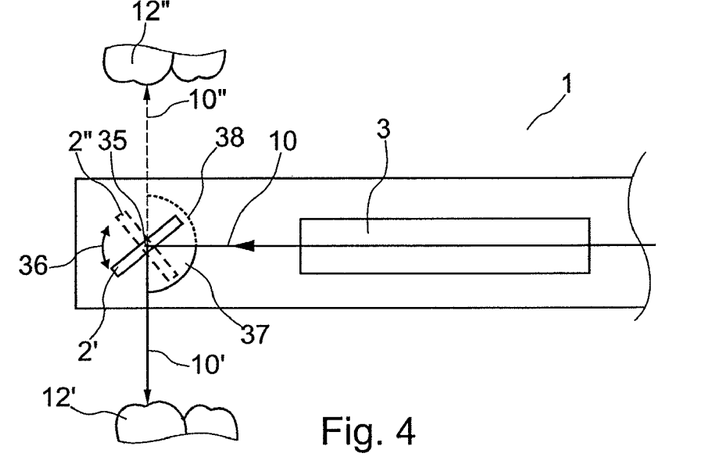
FIG. 4 is a detailed view of the apparatus shown in FIG. 1 comprising a first beam deflector which can be shifted between two positions.

FIG. 4 shows an apparatus 1 comprising a first beam deflector 2, which can be shifted between two positions 2' and 2" about the axis 35 by a rotating movement 36. In the first position 2', the first beam deflector 2 in the form of a deflection mirror deflects the illuminating beam 10 in a first direction 10' to the teeth of the lower jaw 12' and in the second position 2" to the teeth of the upper jaw 12". The apparatus 1 thus need not be turned in order to switch from 3 D measurement of the lower jaw 12' to 3 D measurement of the upper jaw 12". The first direction 10' is at a first angle 37 of 90° and the second direction 10" is at a second angle 38 of 90° relative to the illuminating beam. This angle 37 might range from 5° to 175°.

Figure 5:
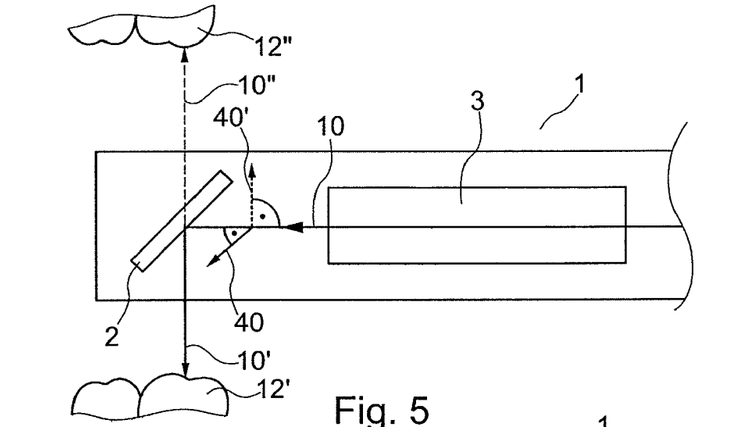
FIG. 5 is a detailed view of the apparatus shown in FIG. 1 comprising a beam deflector which deflects the illuminating beam according to its polarity.

FIG. 5 shows an apparatus 1 comprising a beam deflector 2, which deflects the illuminating beam 10, depending on the direction of polarization, either in the first direction 10' to the teeth of the lower jaw 12' or in the second direction 10" to the teeth of the upper jaw 12". In a first direction of polarization 40, the illuminating beam 10 is deflected in the first direction 10' and, in a second direction of polarization 40', in the second direction 10". Such a polarization-dependent beam deflector can, for example, consist of a polarizing filter and a deflection mirror disposed downstream thereof in the optical path of the illuminating beam 10. If the direction of polarization 40 of the illuminating beam 10 is at right angles to the transmission direction of the polarizing filter, the illuminating beam 10 will be reflected almost entirely by the polarizing filter and deflected in the first direction 10'. If the polarization 40' of the illuminating beam 10 is parallel to the transmission direction of the polarizing filter, the illuminating beam will pass therethrough almost entirely and will then be reflected by the deflection mirror disposed downstream of the polarizing filter and deflected in the second direction 10".

Figure 6:
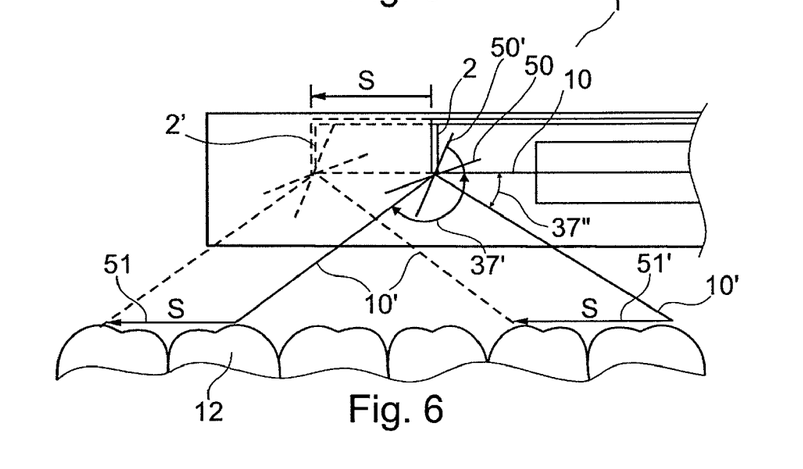
FIG. 6 is a detailed view of the apparatus shown in FIG. 1 comprising a first beam deflector, the angle of which can be adjusted relatively to the direction of the illuminating beam.

FIG. 6 shows an apparatus 1 comprising a first beam deflector 2, the angle 50 of which relative to the direction of the illuminating beam 10 can be varied. The first beam deflector is shown in two angular positions in which a first angle 50 is 20° and a second angle 50' is 65°. Consequently, an angle 37' of 140° is formed between the illuminating beam 10 and the deflected illuminating beam 10' when the first beam deflector is in the first angular position at an angle 50 of 20°, and an angle 37" of 50° is formed when the beam deflector is in the second angular position at an angle 50' of 65°. When the first beam deflector 2 is moved linearly from a first position 2 in the longitudinal direction of the apparatus 1 over a path distance S to a second position 2', a scan area 51 of length S is scanned in the first angular position at an angle 50, and a scan area 51' is scanned in the second angular position at an angle 50'. It is thus possible to scan a scan area which is disposed in front of the apparatus and is difficult to access, such as the region of the molars, for example.

LIST OF REFERENCE NUMERALS

1 apparatus
2 first beam deflector
2' first beam deflector moved through distance S
3 objective
3' objective moved through distance S
4 connector
5 fiber-optic light guide
6 base unit
7 light source
8 beam splitter
9 image sensor
10 illuminating beam
10' first direction
10" second direction
11 surface, surface of tooth
12 of object to be measured, tooth
12' in lower jaw
12" in upper jaw
13 monitoring beam
14 focal point
15 scan area
16 housing
20 force-balancing unit
21 counterweight
22 guide means
23 scanning unit
24 beam deflector
25 beam deflector
26 guide means
27 toothed wheel
28 toothed rack
29 toothed wheel
30 toothed rack
31 driving toothed wheel
32 toothed rack 33 toothed rack
34 connecting part
35 axis
36 turning movement
37 first angle
38 second angle
40 first direction
40' second direction
50 angle
50' second angle
51 scan area
51' scan area
S path distance
$F_1$ acceleration force of the scanning unit
$F_2$ acceleration force of the counterweight
$M_1$ torque of the scanning unit
$M_2$ torque of the counterweight
D fulcrum
$r_1$ distance
$r_2$ distance

The invention claimed is:

1. An apparatus for optical 3D measurement, comprising a first beam deflector for deflecting an illuminating beam onto an object to be measured and for deflecting a monitoring beam reflected from the object to be measured, wherein said first beam deflector is displaceable along a path distance S, and wherein a counterweight in a force-balancing unit can be moved contrarily to the motion of said first beam deflector so that the forces and torques arising due to the motion of said first beam deflector and of said counterweight counterbalance each other.

2. The apparatus as defined in claim 1, wherein said counterweight is linearly guided contrarily to the linear motion of said first beam deflector by means of guide means inside said housing of said apparatus.

3. The apparatus as defined in claim 1, wherein motion of said counterweight is coupled to motion of said first beam deflector through coupling means.

4. The apparatus as defined in claim 3, wherein said coupling means consist of toothed wheels, toothed racks, springs, and/or resilient fibers.

5. The apparatus as defined in claim 1, wherein an objective for focusing said illuminating ray can be moved concurrently together with the first beam deflector along said path distance S.

6. The apparatus as defined in claim 5 wherein said objective is a chromatic objective and said illuminating beam is focused as defined in wavelength onto a surface of said object to be measured.

7. The apparatus as defined in claim 1 or claim 5, wherein said beam deflector can be moved along path distance S in an oscillatory manner.

8. The apparatus as defined in claim 7, wherein oscillatory motion of said first beam deflector takes place at a frequency of from 1 Hz to 100 Hz.

9. The apparatus as defined in claim 1, wherein said first beam deflector is linearly guided along path distance S by means of guide means inside a housing of said apparatus.

10. The apparatus as defined in claim 1, wherein the length of said path distance S is between 1 mm and 40 mm.

11. The apparatus as defined in claim 1 wherein said first beam deflector is part of a scanning unit which can be moved in an oscillatory manner within a housing of said apparatus.

12. The apparatus as defined in claim 11 wherein said scanning unit comprises a plurality of beam deflectors, in order to effect multiple deflections of said illuminating beam.

13. The apparatus as defined in claim 11 wherein said scanning unit includes said objective for focusing said illuminating beam onto a surface of said object to be measured.

14. The apparatus as defined in claim 1 wherein said apparatus has a connector for a fiber-optic light guide connecting said apparatus to a base unit, and the fiber-optic light guide passes the illuminating beam from a light source in the base unit to said apparatus and said monitoring beam reflected by said object to be measured is returned to the base unit and is deflected by means of a beam splitter and analyzed.

15. The apparatus as defined in claim 14 wherein said first beam deflector is disposed at an end of said apparatus which is remote from said connector for said fiber-optic light guide.

16. The apparatus as defined in claim 1 wherein said first beam deflector encloses an angle of 45° with said illuminating beam so that the latter is deflected at right angles.

17. The apparatus as defined in claim 1 wherein said illuminating beam consists of a series of component beams disposed in a plane.

18. The apparatus as defined in claim 1 wherein said optical 3D measurement apparatus is a dental handpiece adapted for scanning tooth surfaces in an oral cavity of a patient.

19. The apparatus as defined in claim 1 wherein said first beam deflector can be shifted between two positions, in which a first beam deflector in a first position deflects the illuminating beam in a first direction and in a second position deflects said illuminating beam in a second direction contrary to said first direction.

20. The apparatus as defined in claim 19 wherein with a first direction of polarization, said first beam deflector deflects said illuminating beam in said first direction and, in a second direction of polarization, in said second direction contrary to said first direction.

21. The apparatus as defined in claim 1 wherein said first beam deflector is variable as regards its angle relative to the direction of said illuminating beam.

22. A method for optical 3D measurement implementing an apparatus comprising a first beam deflector, wherein by means of said first beam deflector, which is displaceable within the apparatus along a path distance S, an illuminating beam is deflected onto an object to be measured and a monitoring beam reflected by said object to be measured is deflected back,
wherein a counterweight in a force-balancing unit is moved in an oscillatory manner contrarily to said first beam deflector so that the forces and torques arising from the motion of said first beam deflector and of said counterweight counterbalance.

23. The method as defined in claim 22, wherein said first beam deflector is moved along path distance S in an oscillatory manner.

24. A method for optical 3D measurement implementing an apparatus comprising a first beam deflector, wherein by means of said first beam deflector, which is displaceable along a path distance S, an illuminating beam is deflected onto an object to be measured and a monitoring beam reflected by said object to be measured is deflected back, wherein a counterweight in a force-balancing unit is moved in an oscillatory manner contrarily to said first beam deflector so that the forces and torques arising from the motion of said first beam deflector and of said counterweight counterbalance each other.

25. The method as defined in claim 24, wherein said first beam deflector is moved along path distance S in an oscillatory manner.

26. The method as defined in claim 25 wherein oscillatory motion of said first beam deflector takes place at a frequency of from 1 Hz to 100 Hz.

27. The method as defined in claim 24, wherein said beam deflector is moved linearly along path distance S.

28. The method as defined in claim 24, wherein said counterweight is moved linearly contrary to the motion of said first beam deflector.

29. The method as defined in claim 24 wherein the length of path distance S is between 1 mm and 40 mm.

30. The method as defined in claim 24 wherein said illuminating beam is multiply deflected by further beam deflectors disposed in an optical path distance upstream of said first beam deflector.

31. The method as defined in claim 24 wherein said illuminating beam is focused by an objective onto a surface of said object to be measured.

32. The method as defined in claim 24 wherein said first beam deflector deflects said illuminating beam at right angles.

33. The method as defined in claim 24 wherein said illuminating beam is a radiated polychromatic illuminating beam focused by an objective onto a surface of said object to be measured depending on wavelength.

34. The method as defined in claim 24 wherein said illuminating beam consists of a series of component beams disposed in a plane.

35. The method as defined in claim 24 wherein said object to be measured is a surface of a tooth in the oral cavity of a patient.

36. The method as defined in claim 24 wherein said first beam deflector is shifted between two modi, wherein said first beam deflector in a first mode deflects said illuminating beam in a first direction and in a second mode deflects said illuminating beam in a second direction contrary to said first direction.

* * * * *